US006517886B1

(12) United States Patent
Chau et al.

(10) Patent No.: US 6,517,886 B1
(45) Date of Patent: *Feb. 11, 2003

(54) POSITIVE HYDRATION METHOD OF PREPARING CONFECTIONERY AND THE RESULTING PRODUCT

(75) Inventors: Tommy L. Chau, Fairfax, VA (US); Khoa Nguyen, Centreville, VA (US); Aradhana Sasan, Chantilly, VA (US); Peter King, Herndon, VA (US); Paul Croushorn, Chantilly, VA (US)

(73) Assignee: Biovail Corporation International, Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/609,121

(22) Filed: Jun. 30, 2000

Related U.S. Application Data

(63) Continuation-in-part of application No. 09/580,213, filed on May 26, 2000, now abandoned, which is a continuation-in-part of application No. 08/881,853, filed on Jun. 24, 1997, now abandoned, which is a continuation-in-part of application No. 09/046,186, filed on Mar. 23, 1998, now abandoned, which is a continuation-in-part of application No. 09/092,775, filed on Jun. 5, 1998, now abandoned, which is a continuation-in-part of application No. 09/149,597, filed on Sep. 8, 1998, now abandoned.

(51) Int. Cl.$^7$ .................................................. A23G 3/00
(52) U.S. Cl. ........................ 426/660; 426/658; 426/572
(58) Field of Search ................................. 426/660, 658, 426/572

(56) References Cited

U.S. PATENT DOCUMENTS

| 5,587,198 A | * 12/1996 | Cherukuri et al. ........... 426/660 |
| 5,637,313 A | 6/1997 | Chau et al. ................. 424/440 |
| 5,804,247 A | 9/1998 | Zamudio-Tena et al. |
| 5,928,664 A | 7/1999 | Yang et al. ................. 424/440 |

FOREIGN PATENT DOCUMENTS

| EP | 0155203 | * 9/1985 |
| WO | WO 98/58549 | * 12/1998 |
| WO | WO 99/48379 | * 9/1999 |
| WO | WO 99 62351 A | 12/1999 |
| WO | WO 00 01245 A | 1/2000 |
| WO | WO 00 13522 A | 3/2000 |
| WO | WO 00 13523 A | 3/2000 |

* cited by examiner

Primary Examiner—Nina Bhat
(74) Attorney, Agent, or Firm—Pillsbury Winthrop LLP; Robin L. Teskin

(57) ABSTRACT

The invention provides an uncooked, unspun intimately mixed confectionery composition having sufficient internal cohesively to be handled without losing its integrity as a mass, said composition being substantially free of unbound water and having substantially no phase separation of moisture, containing:(i) a saccharide based component; (ii) a hydrated hydrobinding component having a water activity substantially less than about 0.75, in combination with a humectant, and a (iii) fat component having a melting point substantially in the range of about 28 to about 45 degrees centigrade for providing a soft yet substantially unsticky chew texture for the composition.

14 Claims, No Drawings

POSITIVE HYDRATION METHOD OF PREPARING CONFECTIONERY AND THE RESULTING PRODUCT

This application is a Continuation-In-Part (CIP) application of U.S. co-pending application Ser. No. 09/580,213, which was filed in the U.S. Patent and Trademark Office on May 26, 2000, which is a Continuation-In-Part of:

A. co-pending U.S. application Ser. No. 08/881,853 filed Jun. 24, 1997; and a continuation-in-part of B. co-pending U.S. application Ser. No. 09/046,186 filed Mar. 23, 1998; and a continuation-in-part of C. co-pending U.S. application Ser. No. 09/092,775 filed Jun. 5, 1998; and a continuation-in-part of D. co-pending U.S. application Ser. No. 09/110,713 filed Jul. 7, 1998; and a continuation-in-part of E. co-pending U.S. application Ser. No. 09/149,597 filed Sep. 8, 1998.

FIELD OF THE INVENTION

The present invention relates to confectioneries, and more particularly to a method of producing a confectionery delivery system for actives having the consistency of chewy nougat which is obtained without cooking and without exposing the components of the confectionery to high heat. The invention also relates to the novel confectionery systems produced

BACKGROUND OF THE INVENTION

The present invention relates to the art of unique delivery systems for comestibles, especially to confectionery manufacturing and particularly to novel methods of making a functionalized confectionery mass which do not require cooking to dehydrate and products therefrom. More particularly, the invention relates to comestible delivery systems, uncooked confectioneries and nougats, and methods for making same.

It is generally considered a necessity in the art of preparing food or drug delivery systems like confectionery masses such as nougats to use water as a mixing medium and source of hydration for ingredients. Specifically with respect to nougats, a typical recipe calls for soaking egg albumen in water over a period of time, such as overnight, in order to fully hydrate the protein. Following hydration the egg albumen is stirred and strained before being beaten into a stiff foam. Other ingredients such as sugar, honey, and corn syrup are separately cooked with water to a relatively high cooking temperature of from about 135° C. to about 138° C. to achieve the necessary interaction among the ingredients. The cooked mixture is then poured into the egg and beaten with a nougat mixer, which is similar to a marshmallow mixer but generally more robust. Additional parts of sugar and other ingredients must then be added and the mixture beaten or stirred over a hot water bath. This conventional nougat preparation method requires cooking the ingredients and using a significant amount of water to serve as a mixing medium and source of hydration. The amount of water used is much larger than that which would permit the formation of the solid nougat. Consequently, the excessive moisture must be driven off as much as possible to achieve the structural integrity and consistency necessary for the end product.

Conventional art processes require excessive amounts of water to provide a mixing medium and to hydrate the components. With respect to hydration, water is supplied in more than sufficient quantity to ensure that specific ingredients are wetted and functionalized. With respect to use of water as a mixing medium, once again an excessive amount of moisture is generally used so that ingredients can be contacted by suspension or dissolution in the medium. The overall process requires the use of far more moisture than is actually required to provide solubility of the ingredients. Unless the water is forcibly removed, the process will result in an incoherent product having no significant structural integrity.

A consequence of using excessive water to hydrate and as a mixing medium is that the artisan must then reduce the unwanted additional moisture. This is generally undertaken by a combination of mixing and boiling to drive off the moisture and bring the mass to proper viscosity and consistency. This process, however, can be highly energy-inefficient and very costly as it requires heat, excessive handling of nougat masses, flashing off of some critical fluids, and an inability to incorporate heat sensitive materials, as well as a less desirable overall stability of the product. Moreover, it is not effective in completely eliminating a substantial amount of the moisture contained in the confectionery mass.

One of the unwanted results of inefficient dehydration is that water remains as a separate phase in the end product. This water is not bound to other ingredients and can be referred to as free moisture or unbound water. Free moisture can detract from the end product because it weakens the structural integrity and/or reduces the quality of organoleptic perception. Moreover, excessive free moisture results in higher water activity, and thereby provides an environment in which microorganisms can grow. Microbiological growth in food products has also been used to measure the existence of free moisture.

Free moisture has been identified in food art by the term water activity. Water activity is defined as the ratio of the vapor pressure of water in an enclosed chamber containing a food to the saturation vapor pressure of water at the same temperature. Water activity is an indication of the degree to which unbound water is found and, consequently, is available to act as a solvent or to participate in destructive chemical and microbiological reactions.

Many food preservation processes attempt to eliminate spoilage by lowering the availability of water to microorganisms. Reducing the amount of free moisture or unbound water also minimizes other undesirable chemical changes which can occur in foods during storage. The processes used to reduce the amount of unbound water in foods include techniques such as concentration, dehydration, and freeze-drying. These processes often require intensive expenditure of energy and are not cost efficient.

In addition, the goal of producing an acceptable chewy nougat confectionery has been further complicated by the inclusion of one or more active substances such as bioaffecting agents or nutrients. Many of these substances are not only heat-sensitive, but also possess undesirable organoleptic features in the sense that they are bad tasting, have a disagreeable odor, or are difficult to chew or swallow. Of further complication is the fact that many of these actives are extremely difficult to blend into an edible delivery system. Often they are simply not physically compatible with one or more of the confectionery ingredients.

Various attempts have now been made to formulate acceptable confectionery systems containing actives. For example, Yang et al., U.S. Pat. Nos. 4,778,676, 4,882,152 and 4,882,154, describe a chewable delivery system comprising a gummy confectionery in which an active is first pre-coated with large amounts of oleaginous material.

Chau et al., U.S. Pat. No. 5,637,313, is directed to a soft, chewable dosage form in which maltitol syrup (HSH) must be utilized. The dosage forms are described as chewing gums, hard candy, cough drops and breath fresheners.

Peters et al., U.S. Pat. No. 4,582,709, relates to a chewable mineral supplement in which corn syrup, sugar, an edible polyol, water and a mineral supplement are combined.

Becker, U.S. Pat. No. 4,545,989, describes a chewable comestible product having a frappe component and a syrup component.

Fuisz, U.S. Pat. Nos. 5,804,247 and 5,587,198, are directed to a confectionery system which is formed by first flash-flow processing of saccharide material in a centrifugal spinning machine under high heat conditions. The resultant flash-flow processed material is then admixed with a well-hydrated hydrobinder such as gelatin.

Sharma et al., U.S. Pat. No. 4,797,288, is directed to a drug delivery system including a core material containing an active and a hydrophobic matrix coating.

Shaw et al., U.S. Pat. No. 4,790,991, relates to an ingestible aggregate containing a pre-swelled substantially anhydrous hydrocolloid and a substrate.

Many of the foregoing references, however, have not always proven wholly successful in providing both a suitable confectionery delivery system, and an acceptable, cost-efficient method of production.

The present invention overcomes the difficulties set forth above as well as other difficulties generally associated with the aforementioned art references. In particular, both the necessity of cooking the confection to obtain desired physical properties and using excessive water to mix and hydrate one or more ingredients is eliminated, as is the need to overprocess an unpalatable active. In addition, the method and product of the invention are obtained without any need for subsequent dehydration. Heating at high temperatures and mixing to drive off excessive moisture are no longer required. Consequently, the detrimental heat history generally associated with energy-intensive procedures is also eliminated. Separation of the water from the resulting product is avoided and the lowered water activity results in a product having superior physical, storage, and organoleptic properties with reduced microbial growth problems.

SUMMARY OF THE INVENTION

This application is an improvement of the confectionery taught in the following applications:

U.S. application Ser. No. 08/881,853 filed Jun. 24, 1997, U.S. application Ser. No. 08/773,025 filed Dec. 24, 1996, U.S. application Ser. No. 08/455,936 filed May 31, 1995 now U.S. Pat. No. 5,587,198, U.S. application Ser. No. 09/046,186 filed Mar. 23, 1998, U.S. application Ser. No. 08/770,859 filed Dec. 20, 1996, U.S. application Ser. No. 09/092,775 filed Jun. 5,1998, U.S. application Ser. No. 09/110,713 filed on Jul. 7, 1998, U.S. application Ser. No. 09/149,597 filed Sep. 8, 1998, U.S. application Ser. No. 09/092,775 filed on Jun. 5, 1998, U.S. application Ser. No. 09/046,186 filed Mar. 23, 1998, and U.S. application Ser. No. 08/881,853 filed Jun. 24, 1997.

The present invention includes a method of making a unique food and drug delivery system, and especially a novel confectionery delivery system, in particular a chewy nougat, by a positive hydrating step and without the need for subsequent dehydrating in order to produce the confectionery mass. The present invention also includes the product resulting from the new method of preparation.

In one preferred embodiment, a saccharide-based component is prepared and combined with a hydrated hydrobinding component and a fat component.

A primary part of the saccharide based component is a saccharide material such as sucrose, corn syrup solids, polydextrose, or the and mixtures thereof. Other highly preferred saccharide materials include sucrose and corn syrup solids. Maltodextrin is also highly desirable, as well a s mixtures of any of the foregoing. Preferably, the saccharide-based component is substantially dry, that is without added liquid, e.g. water; or oil.

The hydrated hydrobinding component can include a carbohydrate material such as a carbohydrate syrup such as corn syrup, rice syrup, fructose syrup, or a hydrogenated glucose syrup (HSH) or the like and mixtures thereof in combination with a humactant such as glycerine, propylene glycol or the like. Generally, the carbohydrate syrup imparts viscoelasticity to the confectionery mass. Preferably, the hydrobinding component is further employed with humectant, such as a polyol like glycerin or other commercially available material having similar functionality.

The fat component is required in order to impart a soft yet unsticky chew texture for the confectionery. The fat component helps to slow down the recrystalization of any saccharide structure such as sucrose by disrupting the continuous phase of the saccharide structure present such as sucrose by disrupting the continuous phase of the saccharide structure. The fat component may include hydrogenated vegetable oils, such as coconut oil, partially hydrogenated soybean oil, partially hydrogenated palm kernel oil, partially hydrogenated cottonseed oil or the like or any other vegetable oil or any fat derived emulsifier that exhibits fat mouth feel and texture such as mono or diglycerides or the like, all within the specified range for melting point.

Emulsifiers may also be utilized in the composition such as lecithin or the like.

It is further contemplated that one or more active ingredients can be included in the confectionery mass of the present invention. The active ingredients are typically ones which are intended to produce a biological and/or chemical response in the body. The active ingredients can be quite varied, and a non-exhaustive list has been set forth herein below. Preferred actives include antacid materials or bioassimilable sources of calcium, as well as other actives which also have poor organoleptic properties such as foul taste, gritty mouthfeel or bad odor.

In another preferred embodiment of the present invention a nougat mass is prepared which has a chewy consistency and is made with nutritional ingredients so that a health product can be produced. In particular, protein, vegetable and/or fruit components, including dietary fiber, can be added to provide a nutritious food product. If desired, a product having the minimum daily nutritional requirements can be produced. The recommended human adult dietary serving of nutrients is defined by the Consumer Affairs Division of the United States Food and Drug Administration, the publications of which are incorporated herein by reference. In fact a health bar has been prepared which contains the nutritional equivalent of up to five (5) recommended human adult dietary servings of vegetable and/or fruit. Furthermore in this regard, ingredients which have strong olfactory characteristics, e.g., aroma and flavor, can be treated to enhance control of potency before incorporating into a health product prepared in accordance with the invention.

The product resulting from the present invention is unique because it requires no cooking and no dehydration by traditional heating at high temperatures to produce, and has substantially no phase separation of moisture. The only moisture present is an amount sufficient to functionalize the mass. Thus, the product is fully hydrated.

As herein further described, the product can also be prepared using low or high shear mixing, i.e. with no flash-flow processing required. In other words, the product of the invention may be produced without exposing the components thereof to the high heat and centrifugal forces present in a spinning machine. At the same time, the attributes normally associated with flash-flow processing, e.g. intimate blending of dissimilar ingredients, can still be attained through shear mixing as hereinafter described. It is well known that free moisture in food products can detract from the product. Free moisture has been identified in the art by the use of water activity. In the present invention, the water activity is not greater than about 60% ERH.

Another measure of free moisture in foodstuffs is the amount of biological growth within the composition. In the present invention, the biological activity is less than about 100 ppm, preferably less than about 25 ppm, and most preferably less than about 10 ppm. The addition of the humectant is very important because it ties up any free moisture available thereby lowering the ERH of the finished product to about 60%.

Other features of the method of the invention include improved processing, intimate mixing and enhanced dispersion of dissimilar ingredients. The final product furthermore exhibits improved content uniformity and improved taste perception qualities. In fact, consumers consistently rate the product of the invention higher than many commercially-prepared similar formulations for such qualities as texture, and creaminess, as well as firmness, flavor, bite, sweetness, chewiness, melt characteristics, stickiness, juiciness, freedom from grit, and aftertaste. Overall, the formulated confectionery delivery system herein described is more palatable than many of the current products available in the art.

According to one aspect of the invention there is provided an uncooked, unspun intimately mixed confectionery composition having sufficient internal cohesivity to be handled without losing its integrity as a mass, said composition being substantially free of unbound water and having substantially no phase separation of moisture, comprising:

(i) a saccharide based component;
(ii) a hydrated hydrobinding component having a water activity substantially less than about 75% ERH, in combination with a humectant such as glycerine, propylene glycol or the like, said component being hydrated sufficiently to provide controlled water delivery to the saccharide component to provide only enough moisture to bind the ingredients together when mixed and provide internal lubricity for imbibing, delivering and maintaining the moisture in the mass to provide internal cohesivity without losing its integrity as a mass,
(iii) a fat component having a melting point substantially in the range of about 28 to about 45 degrees centigrade for providing a soft yet substantially unsticky chew texture for the composition wherein component (i) is present substantially between about 16%–75% by weight of said composition, component (ii) is present substantially between about 20%–45% by weight of said composition, and wherein component (iii) is present substantially between about 2%–18% by weight of said composition.

In one embodiment said hydrated hydrobinding component further comprises at least one material selected from the group consisting of a carbohydrate syrup for example corn syrup, rice syrup, fructose syrup, or hydrogenated glucose syrup (HSH) or the like and combinations thereof to impart viscoelasticity to the composition.

Preferably said fat component is selected from the group consisting of hydrogenated coconut oil, partially hydrogenated soybean oil, partially hydrogenated palm kernel oil, partially hydrogenated cottonseed oil or the like or any other vegetable oil or any fat derived emulsifier that exhibits fat mouth feel and texture such as mono or diglycerides or the like, all within the specified range for melting point, and more preferably wherein the fat component blooms to the surface of the composition and provides a shiny finish which minimizes sticking of the composition to equipment and material when handled and packaged. This composition substantially retains its softness over time.

The composition may further comprise a bioactive agent, food, nutritional component, dietary soluble or insoluble fiber, vitamin or mineral for effecting a biological and/or chemical response in the body. For example a mineral additive may be calcium. The calcium is present in an amount of up to about 10% to 40% by weight of said composition, and may be for example calcium carbonate or calcium citrate. or the like.

The composition may also further comprise a cross-linking agent mixed with a hydrobinding agent.

It may also further comprise a further component selected from the group of emulsifiers.

According to yet another aspect of the invention there is provided a method of making an uncooked, unspun intimately mixed composition having sufficient internal cohesivity to be handled without losing its integrity as a mass, the composition being substantially free of unbound water having no phase separation of moisture but which has only enough moisture present to bind the components together, comprising shear mixing together without cooking or spinning:

(i) a saccharide based component;
(ii) a hydrated hydrobinding component having a water activity substantially less than about 75% ERH, in combination with a humectant such as glycerine, propylene glycol or the like said component being hydrated sufficiently to provide controlled water delivery to the saccharide component to provide only enough moisture to bind the ingredients together when mixed and provide internal lubricity for imbibing, delivering and maintaining the moisture in the mass to provide internal cohesivity without losing its integrity as a mass,
(iii) a fat component having a melting point substantially in the range of 28 to 45 degrees centigrade for providing a soft yet substantially unsticky chew texture for the composition wherein component (i) is present substantially between about 16%–75% by weight of said composition, component (ii) is present substantially between about 20%–45% by weight of said composition, and wherein component (iii) is present substantially between about 2%–18% by weight of said composition.

In one embodiment said hydrated hydrobinding component further comprises at least one material selected from the group consisting of a carbohydrate syrup for example corn syrup, rice syrup, fructose syrup, or hydrogenated glucose syrup (HSH) or the like or the like and combinations thereof to impart viscoelasticity to the composition.

In another embodiment said fat component is selected from the group consisting of hydrogenated coconut oil, partially hydrogenated soybean oil, partially hydrogenated palm kernel oil, partially hydrogenated cottonseed oil or the like or any other vegetable oil or any fat derived emulsifier that exhibits fat mouth feel and texture such as mono or diglycerides or the like, all within the specified range for melting point. Preferably the fat component blooms to the surface of the composition and provides a shiny finish which minimizes sticking of the composition to equipment and material when handled and packaged. This composition substantially retains its softness over time.

In another embodiment the method further comprises shear mixing without cooking or spinning a bioaffecting agent into the mixture.

Preferably said bioaffecting agent is untreated and is at least one member selected from the group consisting of a food or nutritional component, dietary soluble or insoluble fiber, vitamin or mineral for effecting a biological and/or chemical response in the body. More preferably said bioaffecting agent is a bioassimilable source of calcium and preferably at least about 10%–40% by weight of calcium.

The calcium may be combined with said saccharide-based component in substantially dry form prior to mixing with said hydrobinding component.

The bioaffecting agent may also be at least one member selected from the group consisting of vitamins, minerals, nutraceuticals, protein and dietary fiber. Preferably the bioaffecting agent is effectively taste-masked by said method.

This method provides for mixing with high shear mixing, low shear mixing, or a combination thereof.

Preferably in carrying out said method said saccharide-based component is high shear mixed with said bioaffecting agent to produce an admixture, said admixture then being low shear mixed with said hydrobinding component.

For a better understanding of the present invention, together with other and further objects, reference is made to the following description taken in conjunction with the examples, and the scope is set forth in the appended claims.

The humectant and preferred glycerine is an important component of the invention in that it enhances the behavior of the finished product by tying up any free moisture which would tend to separate into another phase. The texture therefore, of the finished product is much enhanced by this component and it's addition. The advantages of the humactant in combination with the hydrobinding component is heretofore unknown to provide the improved unsticky nature of the finished product.

DETAILED DESCRIPTION OF THE INVENTION

The method for making confectionery-mass delivery systems in accordance with the present invention includes combining a saccharide-based component and a hydrobinding component, the latter component being hydrated sufficiently to provide controlled water delivery to the saccharide-based component and/or other ingredients to fully functionalize the final mass. Controlled water delivery means delivery of water in an amount and at a rate which is sufficient to provide internal viscosity and cohesivity to the saccharide-based component. The word "hydrated" as used in the term hydrated hydrobound component herein means containing sufficient water to provide the requisite controlled water delivery.

The system created by the combination of the present invention is a water-starved system, which means that the system has only enough moisture to bind the ingredients together and provide internal lubricity. Since the ingredients are competing for moisture due to enhanced wettability, there is virtually no free moisture available to separate from the mass. This activity is provided by the hydrated hydrobinding component. We have also incorporated in our preferred formulation a hydrated hydrobinding agent having a water activity substantially less than 75% ERH having a higher molecular weight than for example simple short chain sugar molecules, which may include a carbohydrate syrup for example corn syrup, rice syrup, fructose syrup, or hydrogenated glucose syrup (HSH) or the like and combinations thereof to impart viscoelasticity to the composition, and preferably in our new formulation corn syrup present in the composition as substantially in the range of 20% to 45% by weight. This preferred carbohydrate syrup component therefore provides for improved viscoelastic chew properties of any finished product. As in the past, no free water is added.

It may also be extremely desirable to utilize high or low shear mixing, hereinafter set forth, to pre-mix the major components prior to combining with one another. It can also be highly preferred to use the aforesaid high or low shear mixing to mix the final composition containing the saccharide-based component and the hydrobinding component so as to yield the confectionery delivery system herein set forth.

As that term is used herein, high shear mixing refers to relatively intensive mixing action concentrated in a localized area. The high speed impact of mixing mechanisms such as blades or choppers results in shearing action. This in turn creates localized high shear force and a fluidizing effect at the point of contact, which causes particular scale diffusion and disagglomeration and faster mixing in a relatively small area of the entire mixing volume. High shear mixing may also result in increased temperature at the point of impact of the shearing apparatus with the mix, thereby further contributing to the effective mixing action.

High shear mixing should be contrasted with low shear mixing in which the main action of mixing is due to the relative motion of a much larger volume of mix being circulated by the spinning or churning action of a lower impact type mechanism, such as a paddle-blade typically found in a Hobart mixer. Whenever high or low shear mixing is utilized to produce the functionalized confectionery mass of the present invention, the resultant product can be referred to as both uncooked and unspun.

As noted, the present invention provides a method and composition for preparing a functionalized confectionery mass without the use of excess water. Functionalization of a confectionery mass means providing the ingredients with sufficient internal cohesivity to be handled without losing its integrity as a mass. In order to be handled in the context of functionalization, the mass must also possess internal lubricity which permits inter- and intra-particle movement without loss of cohesiveness. Functionalized food masses have been described as having the consistency of a dough or paste, or as chewy, etc. However, the present invention is not to be limited by any short-hand description of the consistency.

The composition herein described relies upon the use a fat component, in a predetermined amount having a predetermined range of melting points in order to obtain a confection having desirable perceived texture and/or flavor characteristics.

A functionalized hydrobound confectionery mass of the present invention does not require dehydration, e.g., by cooking at high temperatures, to remove excess water. The method of the invention, therefore, is substantially more efficient than previously known methods. Less energy costs are expended in the methods herein set forth, while the resulting product is a markedly improved confectionery delivery system.

While applicants do not wish to be bound by theory, it is believed that water is tightly bound to surface polar sites through chemisorption. These sites may include the hydroxyl groups of hydrophilic materials such as starches, and sugars. Regardless of the actual mechanism, however, this phenomenon is referred to herein as hydrobinding.

A hydrated hydrobinding component is an ingredient which imbibes, delivers and maintains water in an amount sufficient to functionalize the resulting mass. The water which is hydrobound does not separate and become a separate phase. A hydrobinding component cooperates with other ingredients to deliver and maintain water sufficient to functionalize the mass of ingredients.

Thus, a hydrobinding component can be hydrated and then shear mixed with the ingredients (making up the saccharide based component, and a fat component hereinafter described) to form a functionalized hydrobound confectionery-mass delivery system. After combining the hydrated hydrobinding component and the additional ingredients, moisture is readily imbibed and disseminated throughout the non-hydrated components and/or ingredients. Unlike prior art methods and confectionery compositions, additional moisture is not required to form a hydrated mixture. Thus, excess water is not present in the resulting mass.

The hydrobinding component, saccharide-based component, and fat component acting in concert with one another, capture or bind sufficient moisture to functionalize the total mass. The ingredients capture the moisture by some mechanism as yet unelucidated, possibly physically, chemically, and/or even biologically. Whatever the binding mechanism may be, water is held and made available for absorption by the remainder of the ingredients. The addition of considerable excess water is thus avoided, as is cooking to subsequently drive off the added moisture.

Glycerin or the like is to be included in the composition (or other selected material) typically functioning as a humectant, and thereby keeping moisture in the system. The humectant thus contributes to the successful hydration of the hydrobinding component, and ultimately all components of the final confectionery mass. This enhances the final product.

The invention also employs a saccharide-based material as another major component (the hydrobinding component material being the first major component). The saccharide-based component can include any of a large variety of saccharide materials, such as small sugars, e.g., dextrose, sucrose, fructose, etc., and larger saccharides such as corn syrup solids and polydextrose, as well as mixtures of two or more of these materials.

Corn syrup solids are highly preferred for use as the saccharide-based material in the composition of the invention. Corn syrup solids are commonly known as maltodextrins. Maltodextrins are composed of water soluble glucose polymers obtained from the reaction of the starch with acid or enzymes in the presence of water. The hydrolysis reaction produces a carbohydrate mixture of saccharides having a controllable dextrose equivalent (D.E.), commonly a D.E. of less than 20. When the hydrolysis is permitted to proceed to an extent sufficient to produce a D.E. of greater than 20, the FDA calls the resulting materials corn syrup solids.

Polydextrose is a non-sucrose, essentially non-nutritive, carbohydrate substitute. It can be prepared from polymerization of glucose in the presence of polycarboxylic acid catalysts and polyols. Generally, polydextrose is known to be commercially available in three forms: Polydextrose A and Polydextrose K, which are powdered solids, and Polydextrose N supplied as a 70% solution. Each of these products can also contain some low molecular weight components, such as glucose, sorbitol, and oligomers. Sugars can also be used as saccharide-based materials according to the invention. Sugars are those substances which are based on simple crystalline mono- and di-saccharide structures, i.e., based on $C_5$ (pentose) and $C_6$ (hexose) sugar structures. Sugars include dextrose, sucrose, fructose, lactose, maltose, etc., and sugar alcohols such as sorbitol, mannitol, maltitol, etc. Other saccharide material can include tri-, tetra- and oligosaccharides.

Typically, the foregoing saccharide-based component can comprise about 16–75% of the confectionery delivery system according to the embodiments herein set forth. Preferably, there will be about 18–50% of this component present, and even more desirably about 20–30% present. In addition, those skilled in the art may discover a higher or lower percentage of the saccharide-based component, or other ingredients herein set forth, will produce a suitable final product, depending upon the final characteristics, e.g. texture, mouth feel, product consistency, etc., which are desired.

Preferably, the saccharide-based component is substantially dry, i.e. is in non-liquid form and is without added moisture, e.g. water. It has now been found that while materials such as sugar alcohols and aqueous-based saccharide formulations may be utilized herein, it is best that their presence is at least kept to a minimum in most embodiments. The addition of too much liquid-based saccharide component may cause the final confectionery mass to be too gooey, sticky, tacky and/or gummy, and therefore highly unsuitable for processing, handling, and consuming.

Other materials which can be incorporated into the confectionery mass of the invention, to enhance its appearance, taste, texture, and other perceptions of the consumer, include, for example, flavors, sweeteners, colorants, surfactants or emulsifiers, and fats or oils. Any one or a combination of more than one of the foregoing may comprise from about 0–20% of the confectionery mass, and more desirably be within the range of about 5–10% or even up to 15% of the comestible mass.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combination thereof. A non-limiting representative list of examples includes citrus oils such as lemon, orange, grape, lime, and grapefruit, as well as fruit essences including, for example, apple, pear, peach, grape, strawberry, raspberry, cherry, plum, pineapple, apricot, or other fruit flavors.

Other useful flavorings include, for example, aldehydes and esters such as benzaldehyde (cherry, almond), citralm, i.e., alphacitral (lemon, lime), neural, i.e., betacitral (lemon, lime) decanal (orange, lemon), aldehyde $C_8$ (citrus fruits), aldehyde $C_9$ (citrus fruits), aldehyde $C_{12}$ (citrus fruits), tolyl aldehyde (cherry, almond), 2,6-dimethyloctanal (green fruit), and 2-dodecenal (citrus, mandarin), mixtures thereof, and the like. Other flavorings may include whole and partial fruits and nuts, peanut butter, candy bits, chocolate chips, bran flakes, etc.

Sweeteners may also be added to the confectionery delivery system of the invention. These are typically included to enhance the flavor and impart a palatable sweetness to the confectionery mass. The sweeteners may be chosen from the following non-limiting list and may be added in addition to the saccharide-based component materials: glucose, dextrose, invert sugar, fructose, and mixtures thereof saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof. Other sweeteners may also be used. The sweeteners are added in amounts equal to about 0–10% of the composition, and preferably about 0.1–5%.

Surfactants or emulsifiers may also be included in the composition of the invention. These may be any food grade emulsifying material, for example, lecithin or other phospholipid material, monoglycerides and/or diglycerides, and mixtures thereof in amounts of from about 0–3%, more desirably about 0.1–1%.

Fats are to be included in the composition, and these may include hydrogenated fats such as coconut oil, partially hydrogenated soybean oil, partially hydrogenated palm kernel oil, partially hydrogenated cottonseed oil or the like or any other vegetable oil within the specified range for melting point.

Hard fats have a melting points above body temperature (37.6° C.), and soft fats have a melting point of about or below body temperature, can be used alone or in combination. The texture and mouth feel of the resulting confection can be influenced by selecting the types and amounts of fats included in the composition. Thus, fats will comprise about 2–18% of the product herein set forth. Oils are highly preferred over fats because of their liquid nature which makes them easier to blend with the other ingredients of the invention. Alternatively any fat derived emulsifier that exhibits fat mouth feel and texture such as mono or diglycerides or the like may be utilized.

Additional materials which can be incorporated into the composition of the invention include, for example, biologically active ingredients such a s medicinal substances, e.g. drugs, pharmaceuticals and antacids. These are referred to herein as active ingredients or bioaffecting agents. Active ingredients may make up from about 0–50% of the product of the invention, desirably from about 0.1–50%, and may be more depending upon the needs and abilities of those skilled in the art. It is preferred, however, to include at least about 20%, more preferably about 25%, and even more desirably up to about 40% of one or more active ingredients in the compositions set forth herein.

As active ingredients, the medicinal substances capable of incorporation and delivery according to the invention are extremely varied (those skilled in the art may conceive of others than those herein described, and these are certainly within the scope of the invention). An exemplary, non-limiting list of such medicinal substances includes: antitussives, antihistamines, decongestants, alkaloids, mineral supplements, laxatives, vitamins, e.g. vitamin D3, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and antithyroid preparation, diuretics, antispasmodics, uterine relaxants, mineral and nutritional additives, antiobesity drugs, anabolic drugs, erythropoietic drugs, antiasthmatics, cough suppressants, cold remedies, mucolytics, antiuricemic drugs, nicotine and mixtures thereof.

Analgesics include, for example, aspirin, acetaminophen, and acetaminophen plus caffeine.

Other preferred drugs for other preferred active ingredients for use in the present invention include, for example, antidiarrheals such as IMMODIUM AD®, antihistamines, antitussives, decongestants, vitamins, and breath fresheners. Also contemplated for use herein are anxiolytics such as XANAX®; antipsychotics such as clozaril and HALDOL®; non-steroidal anti-inflammatories (NSAIDs) such as VOLTAREN® and LODINE®, antihistamines such as SELDANE®, HISMANAL®, RELAFEN®, and TAVIST®; antiemetics such as KYTRIL® and CESAMET®; bronchodilators such as BENTOLIN®, PROVENTL®, antidepressants such as PROZAC®, ZOLOFT®, and PAXIL®; antimigraines such as IMIGRAN®, ACE-inhibitors such as Vasotec, Capoten and Zestril; anti-Alzheimer's agents, such as NICERGOLINE; and $Ca^{H}$-Antagonists such as PROCARDIA®, ADALAT®, and CALAN®.

The popular $H_2$-antagonists which are contemplated for use in the present invention include cimetidine, ranitidine hydrochloride, famotidine, nizatidine, ebrotidine, mifentidine, roxatidine, pisatidine and aceroxatidine.

Other active ingredients include antiplaque medicaments and medicaments for veterinary use.

Especially preferred active ingredients contemplated for use in the present invention are antacids, $H_2$-antagonists, and analgesics. For example, antacid dosages can be prepared using the ingredients calcium carbonate ($CaCO_3$),either alone or in combination with magnesium hydroxide, and/or aluminum hydroxide. Moreover, antacids can be used in combination with $H_2$-antagonists.

Active antacid ingredients include, but are not limited to, aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium oxide, magnesium trisilicate, milk solids, aluminum monobasic or dibasic calcium phosphate, tricalcium phosphate, potassium bicarbonate, sodium tartrate, sodium bicarbonate, magnesium aluminosilicates, and tartaric acids and salts.

Calcium supplement products can also be prepared by incorporation of a bioassimilable calcium source in the comestible delivery system confectionery of the invention. Typically, calcium supplements require a larger addition of calcium than do antacids. Preferably, the calcium source is calcium carbonate, but other sources of calcium capable of absorption or bioassimilation can be employed, including finely divided bone meal or oyster shell materials and the like. The calcium-containing material i s preferably very finely divided so as not to impart any unnecessary chalkiness or other unpalatable characteristic to the confection. Moreover, the calcium is preferably provided in substantially dry form; that is, is not pre-treated or pre-coated in a separate step with a liquid such as water or an oleaginous substance, such as wax or oil. Applicants have discovered that "dry" calcium can be more intimately and easily dispersed throughout the resultant confectionery mass. Finely ground calcium materials are commercially available, e.g., from Specialty Minerals, for use either in the antacid products or calcium supplement products. In one preferred embodiment of the invention, a calcium supplement product is prepared which incorporates 500 mg. Of bioassimable calcium, along with 200 I.U.'s of vitamin D3 into a single dosage form of the final product, which represents 50% of the RDA of those nutrients.

In an especially preferred embodiment of the invention, a calcium source may be combined with a magnesium source to yield a mineral supplement "active" included in various embodiments of the chewy nougat formulation. Magnesium has been recognized as an essential element which aids in metabolism. Magnesium also aids in the absorption of calcium, and is therefore highly desirable as an additional component of a chewable, nougat calcium supplement formulation. Any bioassimilable magnesium source may be utilized. Non-limiting examples include those selected from the group consisting of magnesiums oxide, hydroxide, phosphate, carbonate and lactate, for example. Of these, magnesiums oxide, carbonate and lactate are more preferred. Magnesium lactate is desirable because it is highly stable for extended periods, and its inclusion in a chewy supplement imparts very little or and color, flavor, sweetness or textural off-notes thereto. These attributes may be particularly important from a commercial point of view.

An especially preferred dietary supplement therefore includes about 500 mg. of bioassimable calcium, about 40 mg. magnesium, and about 200 I.U.'s of Vitamin D3 into a single dosage form. This represents 50% of the RDA for these nutrients. More or less of the foregoing nutrients may be added, depending upon the particular needs of the skilled artisan. For example, a proportional scale-up or down of the foregoing substituents could be utilized to yield a formulation having, for example, 75%, 100% or even 25% of the foregoing nutrients.

It is certainly within the scope of the invention to include in a chewy nougat dietary supplement from about 20–40% of a calcium source, about 0–5% of Vitamin D3 and about 0–50% of a magnesium source. More preferably, at least about 23–40% of a calcium source, about 1–5% of Vitamin D3, and about 1–20% of a magnesium source may be included in the chewy nougat dietary supplement heretofore described.

The products according to the various embodiments of the invention are tasty and sweet chewy nougat confectioneries, with a smooth texture and consistency, with no grit or chalkiness. These products are well hydrated, and yet evidence no phase separation of moisture upon extended periods of storage. They are therefore extremely suitable for marketing on a large commercial scale.

One of the advantages of the present invention is that a large proportion of the product can be displaced by a bulky material, such as for example calcium sources. For example, it is preferred that up to about 25–35% or even more of the total weight of the resulting product can be an added bioassimilable calcium source, without imparting undesirable taste or texture to the product. In fact, the product according to several embodiments of the invention exhibits improved taste and texture characteristics as compared with similar commercially-available products. "Improved" means that individual consumers rate the product overall to be superior when such characteristics as texture and creaminess as well as firmness, flavor, bite, sweetness, chewiness, melt characteristics, stickiness, juiciness, freedom from grit, and aftertaste are analyzed. Thus, while the product of the invention may contain as much as one-quarter or even more of an unpleasant active such as calcium, it still exhibits a smooth, nougat texture and taste very similar to, or virtually indistinguishable from that of a confectionery such as a tootsie roll or Charleston chew. (Of course, useful comestible delivery systems can also be produced wherein as little as only a trace amount of the total weight of the product is a deliverable active ingredient.).

Another active component which can be included in products made in accordance with the present invention is a nutritional component. A nutritional component can include ingredients such as vitamins and minerals required to maintain good health. A health bar product has been prepared in accordance with the present invention which includes a dry residue of whole vegetables and/or fruits. In fact, a health bar product has been made which includes the nutritional equivalent of up to five (5) times the U.S. recommended human adult dietary serving of vegetables and/or fruit by incorporation of the dry residue of such fruits and vegetables. Other bulky materials can also be included, e.g., dietary fiber, in the confectionery delivery system of the invention.

A preferred embodiment of the nutritional form of the product contemplates treating ingredients having strong olfactory characteristics, e.g., flavor and aroma, to reduce such characteristics. For example, dry residue of spinach and broccoli have been treated by heating in the presence of yogurt powder and a small amount of moisture to drive off strong aroma and flavor notes. This technique conditions such ingredients for incorporation in a health product without detracting from the overall smell and taste of the product. It has been found that the above technique is particularly effective for preparing a nutritional health bar product.

Another nutritional component can include protein from animal and/or vegetable sources (to be distinguished from the proteinaceous material utilized in the hydrobinding component), either alone or together with soluble and/or insoluble dietary fiber, as well as one or more vitamins and minerals.

Also the following may be included as active ingredients including such naturally-derived products as botanical substance extracts, which may include certain derivatives of plants and herbs, as for example, bark, seeds, stem, leaves, roots, berries and flowers. The botanical extracts would much desirably be those which are recognized for their natraceutical properties. Non-limiting examples of these botanical substance extracts could include ginseng, ginkoba, gingko biloba, St. John's wort, and the like. One source of these materials may be found under the brand name STAND-EX™ from Bio-Botanica, Inc., including Lipo Chemicals.

In one desirable embodiment of the invention, the confectionery composition of the invention also includes at least one member selected from the group consisting of vitamins A, B complex (including B1, B2, B6, B12 and biotin), C, D and E.

The product resulting from the present invention is unique because it requires no cooking and no dehydration by traditional heating at high temperatures to produce, and has substantially no phase separation of moisture. The only moisture present is found therein in an amount sufficient to functionalize the mass. Thus, the product can be prepared without cooking.

As heretofore set forth, the chewy confectionery composition herein set forth can also contain one or more other active substances which until now could not be easily administered via a chewable delivery system because of their relatively poor organoleptic properties. These biological and chemical substances are fairly unpleasant looking, tasting or smelling, have a disagreeable mouthfeel, or are otherwise difficult to swallow. Chewing would normally only exacerbate the unpleasantness. The unique confectionery system herein provided effectively taste masks many or all of these substances, and thereby functions as a unique delivery system for these actives. Thus, it is clearly within the scope of the invention to provide a confectionery system containing all types of "unpleasant" actives which can be easily masticated and swallowed like any nougat-type candy. These compositions are sweet-tasting and therefore are easily administered. At the same time, the heretofore described components constituting these formulations effectively taste-mask the bitterness and bad taste associated with these myriad drugs, food substances and nutraceuticals.

One such active as part of the invention is caffeine. The drug itself has long been recognized as enhancing alertness. It can be provided as a nutritional supplement for those who wish to remain awake and cognizant for extended periods. Unfortunately, caffeine is an extremely bitter tasting whitechemical compound, and therefore is not a likely candidate for inclusion in a chewy confectionery formulation. As part of the composition of the invention, however, it is rendered into an extremely delicious, chewable form with excellent mouthfeel. The chewy confectionery herein described thus functions as a delivery system for the caffeine, as well as for other active substances. When included, a dosage of caffeine within the range of about 0.1 to 500 mg is recommended. Preferably, a single serving should contain about 10 to 150 mg of caffeine. It is especially desirable to include about 25 to 100 mg. in a single dose. On a weight basis, any caffeine will typically make up about 0.1 to 5% of the final composition of the invention, and more desirably be within the range of about 0.5 to 2%. These amounts can vary, depending upon the desires of the particular skilled artisan.

The hydrobound system of the present invention is a mass which has been hydrated by adding moisture to provide hydrocolloidal stability, but which does not have measurable free water, e.g., syneresis is substantially halted.

Syneresis refers to as the phenomenon of separation of water from a mass of material as a distinct phase. When the moisture in a mass or sufficiently bound to other components in the mass that phase separation does not occur, syneresis is stopped or halted. When syneresis occurs, free water is available within the system. Free water is generally unwanted in confectionery products of the type disclosed herein because of product deterioration and microorganic growth. A correlation between free water and water activity has been made as a measure of product stability.

A well-known method for characterizing the presence of water is by water activity. Water activity is measured as the ratio between the vapor pressure of water in an enclosed chamber containing a food and the saturation vapor pressure of water at the temperature. Water activity indicates the degree to which water is bound and, subsequently, available to act as a solvent or participate in destructive chemical and microbiological reactions.

When the water activity is low, water is unavailable because it is tightly bound to surface polar sites through chemisorption. Water activity is defined as:

$$a_w = \frac{p}{P_0}$$

where $a_w$ is water activity, p is the partial pressure of water above the sample, and $P_0$ is the vapor pressure of pure water at the same temperature (must be specified).

Another definition of water activity which is more thermodynamically appropriate is $$a_w = \frac{P_{eq}}{P_0}$$

where $P_{eq}$ is the partial vapor pressure of water in equilibrium with the solution and $P_0$ is the vapor pressure of pure water at the same temperature and pressure as the solution. When a solute is added to water, water molecules are displaced by solute molecules and the ratio of the vapor pressures or $a_w$ is altered. Entropy is also lowered as solute molecules become oriented to water molecules. As a result, water molecules are not as free to escape from the liquid phase and the vapor pressure is therefore decreased. This change is governed by Raoult's law, which states that the decrease in vapor pressure of a solution is equal to the mole fraction of its solute. Similarly the ratio of vapor pressures ($a_w$) is governed by the number of moles of solute ($n_1$) and solvent ($n_2$):

$$a_w = \frac{P}{P_0} = \frac{n_1}{n_1 + n_2}$$

Different solutes tie up or bind water to varying degrees depending on the nature of the solute, such as its level of dissociation, extent and nature of intramolecular binding, solubility and chemical components.

Further, a portion of total water content present in foods is strongly bound to specific sites on the chemicals that comprise the foodstuff. These sites may include the hydroxyl groups of polysaccharides, the carboxyl, amino groups of proteins, and other polar sites that may hold water by hydrogen bonding or other strong chemical bonds. In addition to strongly bound water molecules, some of the water in foods is usually bound less firmly but is still not available as a solvent for various water-soluble food component. Thus, water activity is low when water is tightly bound to surface polar sites through chemisorption. The sites can include hydroxyl groups of hydrophilic material which are effective in controlling water activity.

Another measure of free water in foodstuffs can be provided by the amount of biological growth within the composition. In the present invention, the biological activity is less than about 100 ppm, preferably less than about 25 ppm, and most preferably less than 10 ppm.

It is therefore particularly preferred to use the aforementioned low and high shear mixing processes to prepare the product of the invention according to its various embodiments. In this way, the added time and expense associated with other methods of processing can be avoided. The same qualities associated with the final product which can be attained with flash-flow processing can now also advantageously be attained through the use of shear mixing methods.

Thus, the hydrobinding component can be hydrated and then high and/or low shear mixed with the saccharide-based component (the latter also being prepared as a result of low or high-shear mixing) in order to form a fully functionalized hydrobound confectionery mass. After combining the hydrated hydrobinding component and the saccharide-based component, moisture is readily imbibed and disseminated throughout the non-hydrated components and/or ingredients. Again, unlike prior art methods and confectionery compositions, additional moisture is not required to form a hydrated mixture. Thus, excess water is not present in the resulting mass.

Other materials, as heretofore outlined, can be incorporated into the saccharide-based component or the hydrobinding component including, for example, flavors, sweeteners, colorants, surfactants or emulsifiers. Any of the adjunct materials described herein above can be included in the preparation of a suitable product with shearform matrix characteristics.

As heretofore noted, it has now been discovered that the same attributes in the final product of prior art formulations, e.g. intimate mixing, can now also be attained by shear mixing, such as high or low shear mixing, of the saccharide-based component and other materials such as actives, prior to combining with the hydrated hydrobinding component, and the fat component, again using shear mixing. In some instances, a combination of flash-flow process and shear mixing may be utilized to produce the product of the invention. For example, certain ingredients making up the saccharide-based component may be subjected to flash-flow procedures (such as pre-flash-flow processing) in order to combine them. However, any flash-flow processing is best kept to a minimum. Once combined, the saccharide-based component can then be shear mixed with the hydrated hydrobinding and fat components to produce the food and/or drug delivery system of the invention.

It has been further discovered that hydrating the hydrobinding component before mixing with the other components is a much more preferred method of combining ingredients than is simply random mixing, or a method of combining in which all components are immediately dumped together in a shear mixing apparatus. Without being bound by any particular theory, it seems that by hydrating the hydrobinding component separately, and then combining that component with the other components, the necessary hydration and functionalization of the resultant mass is much more effectively attained.

An especially preferred high-shear mixer for use with the invention is known as a Littleford FKM 1200. This device provides high shear mixing by proximal shearing blades which are at right angles to one another. The shearing blades consist of "plowers" and choppers, both of which are utilized for high shear mixing action. While not wishing to be bound by any particular theory, it is believed that high shear action provides both mixing and heating at the localized points of blade contact with the mix ingredients, thereby resulting in excellent dispersibility without the undesired effects of lumping etc. Other high shear mixers (with one or more mixing blades), currently available or yet to be developed, are also contemplated by the method of the invention.

If desired, the high shear mixer can be further equipped with a jacket heater to provide the benefits of additional warming (but not cooking). A preferred temperature range for warming is therefore from about 30 degrees C. to about 60 degrees C., more desirably within the range of about 30 degrees to about 45 degrees C.

A preferred procedure for high shear mixing the composition of the invention is as follows: The jacket heater on the high shear mixer is first activated and allowed to warm to a temperature of about 40 degrees C. Next, the saccharide-based component and other dry ingredients, e.g. calcium carbonate, are fed through the open hopper and allowed to mix using the plowers. For an 18 pound mixture, for example, the device is first run for about 2 minutes. The fat component is then added, along with emulsifiers, and the liquid-based hydrobinding component (together with any flavorings, sweeteners and coloring) are then fed into the mixer, and the choppers or high shear blades are activated to further complete the mixing. During this time, the jacket temperature may be increased to within the range of about 50–60 degrees C., preferably about 58–60 degrees to assist in the mixing. The mixer is then run for about 5–10 minutes more, perhaps longer, to complete the mixing of the saccharide-based component and the hydrobinding component. Once mixing is complete, the entire matrix is then emptied into an appropriate container for slicing, sorting and shipping etc., e.g. is extruded and cut into dosage size pieces.

In certain preferred embodiments, the use of a low shear mixing apparatus can also provide the product of the invention. Of these, a Sigma mixer and/or Hobart industrial paddle mixer may be suitable. In one preferred embodiment, the dry ingredients (saccharide-based component and any additional materials, e.g. one or more actives) are mixed in a Sigma mixer until a good consistency is obtained. Separately, the liquid ingredients (hydrobinding components) are mixed in a Hobart mixer, and then added to the Sigma mixer with the dry ingredients. The whole mixture is then run in the Sigma mixer for about 3 minutes. Variations of the foregoing process are certainly within the scope of the invention, depending upon the characteristics of the individual ingredients, and the attributes desired within the final product. The goal is to achieve enhanced hydration and intimate mixing of all ingredients so that the final confectionery is a chewy, nougat-type confectionery with a good mouthfeel in which any unpleasant smell or taste perceptions which may b e associated with the "raw" ingredients is effectively masked.

Another method of formulating the product of the invention utilizes both high- and low-shear mixing apparatus. Dry ingredients such as corn syrup solids and sucrose (polysaccharide component) are first mixed together with other dry ingredients, e.g. calcium carbonate, as well as the fat-based component and any emulsifier(s), in a high shear mixer, preferably a Littleford FKM 1200, according to the procedure described above (plowers first, followed by shearing blades for about 5–10 minutes). Next, in a low shear mixer (e.g. Hamilton) the liquid ingredients, i.e., the hydrobinding component along with any optional, additional sweeteners, flavorings, colors and if desired, vitamin D3 formulation dissolved in corn syrup, are mixed together for a few minutes. This resulting mixture is then added to the dry mix (which has now been transferred from the high shear mixer to another low shear mixer, e.g. Guittard). All ingredients are then mixed in this second low shear mixer for a few more minutes (~3 minutes), with the resulting mass then sent through an extruder for final processing such as slicing, sorting and shipping, etc.

In still another embodiment of the method of the invention, the saccharide-based component along with the calcium carbonate and vitamin D3 are first mixed together in the high shear mixer. The resulting formulation is then added to an extruder together with the liquid ingredients (hydrobinding component) for final mixing, and extrusion. The extruder would of course be of the type known in the art which is adapted to receive liquid components.

Through the use of or shear mixing the need to cook the confectionery product of the present invention is thus eliminated. Also, the need to spin the material can also be preferably eliminated.

For a better understanding of the present invention, together with other and further objects, the following examples and tables are provided to illustrate the unique methods of making a confectionery mass and products resulting therefrom. Unless otherwise specified, percentages of components in the compositions are given as percentage by weight (wt %). Also, unless otherwise indicated, all materials were obtained from commercial suppliers.

The following examples serve to illustrate various embodiments of the invention, but in no way should they be construed as limiting the scope thereof.

EXAMPLE 1

A series of confectionery-type masses was prepared according to the invention, for the delivery of a bioassimilable calcium source, in this case dry powdered calcium carbonate. The hydrobinding material was selected to be corn syrup. The saccharide-based material was selected to b e sucrose (6×) or a mixture of sucrose and corn syrup solids. The fat component is hydrogenated coconut oil. The components and the preparation conditions for these batches are given below in Table 1. The batch size in the examples is 2 kg. A sigma mixer was used to prepare the final products.

The following information is provided by way of example and is not to be considered restrictive in any sense to the interpretation of the breadth of this invention.

EXAMPLES

1. Laboratory Process Description—Chocolate Calcium Soft Chew

A. Heat corn syrup to 55±5° C. and stir in glycerin.
B. Combine calcium carbonate, sugar, cocoa powder, vitamin $D_3$ premix, and flour salt. Mix in sigma mixer for 5 minutes. Add flavors while mixing.
C. Heat coconut oil to 40±5° C. to melt. When melted, stir in lecithin. Add to milk solids in a food processor and mix for 1 minute.
D. Add A & C to B and mix in sigma mixer for 5 minutes or until completely blended. It will be useful to run the mixer in reverse for a minute to aid mixing. Target temperature is 35±5° C.
E. Remove D from sigma mixer and place in a labeled polyethylene bag. The product will be soft and sticky. Roll out until it is of a uniform thickness and consistency. Let sit overnight and evaluate next day.

Note: It may be desirable to premix certain items for use in manufacture.

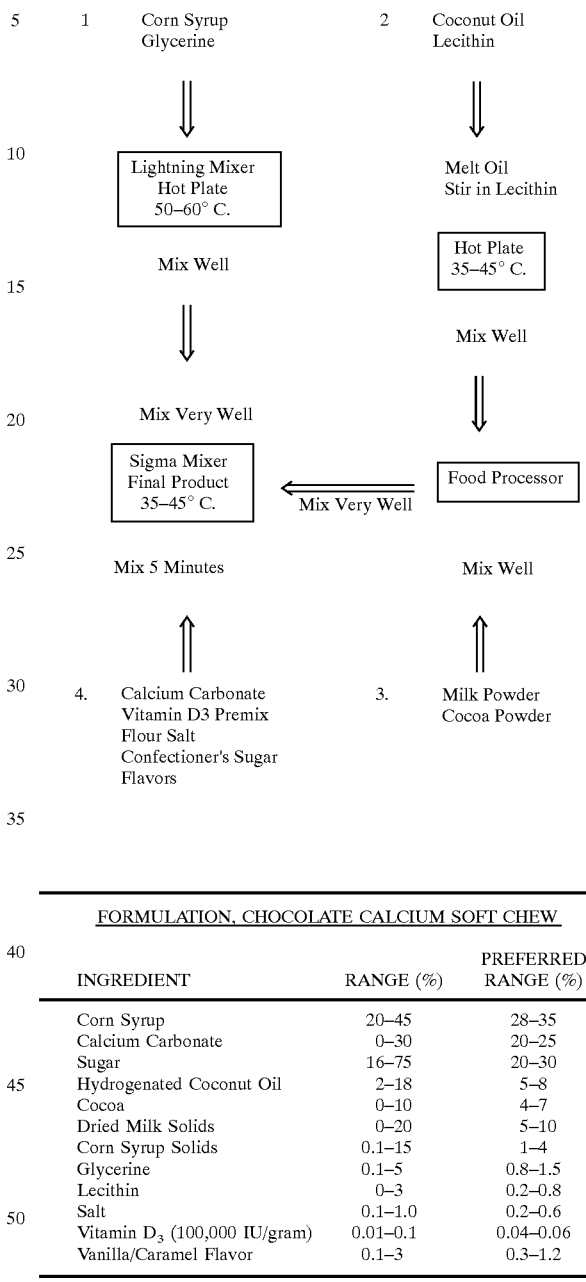

Process Flow Diagram
Chocolate Calcium Soft Chew

| FORMULATION, CHOCOLATE CALCIUM SOFT CHEW | | |
|---|---|---|
| INGREDIENT | RANGE (%) | PREFERRED RANGE (%) |
| Corn Syrup | 20–45 | 28–35 |
| Calcium Carbonate | 0–30 | 20–25 |
| Sugar | 16–75 | 20–30 |
| Hydrogenated Coconut Oil | 2–18 | 5–8 |
| Cocoa | 0–10 | 4–7 |
| Dried Milk Solids | 0–20 | 5–10 |
| Corn Syrup Solids | 0.1–15 | 1–4 |
| Glycerine | 0.1–5 | 0.8–1.5 |
| Lecithin | 0–3 | 0.2–0.8 |
| Salt | 0.1–1.0 | 0.2–0.6 |
| Vitamin $D_3$ (100,000 IU/gram) | 0.01–0.1 | 0.04–0.06 |
| Vanilla/Caramel Flavor | 0.1–3 | 0.3–1.2 |

2. Laboratory Process Description—Vanilla Calcium Soft Chew

A. Heat corn syrup to 55±5° C. and stir in glycerin.
B. Combine calcium carbonate, confectioners sugar, vitamin $D_3$ premix, and flour salt. Mix in sigma mixer for 5 minutes. Add flavor while mixing.
C. Heat coconut oil to 40±5° C. to melt. When melted, stir in lecithin. Add to milk solids in a food processor and mix for 1 minute.
D. Add A & C to B and mix in sigma mixer for 5 minutes or until completely blended. It will be useful to run the mixer in reverse for a minute to aid mixing. Target temperature is 30±5° C.
E. Remove D from sigma mixer and place in a labeled polyethylene bag. The product will be soft and sticky. Roll out until it is of a uniform thickness and consistency. Let sit overnight and evaluate next day.

Note: It may be desirable to premix certain items for use in manufacture.

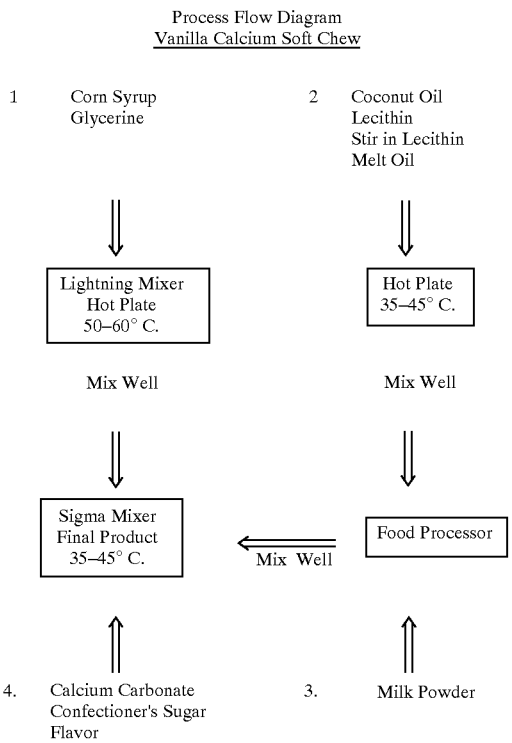

Process Flow Diagram
Vanilla Calcium Soft Chew

| FORMULATION, VANILLA CALCIUM SOFT CHEW | | |
|---|---|---|
| INGREDIENT | RANGE (%) | PREFERRED RANGE (%) |
| Corn Syrup | 20–45 | 28–35 |
| Calcium Carbonate | 0–30 | 20–25 |
| Sugar | 16–75 | 20–30 |
| Hydrogenated Coconut Oil | 2–18 | 5–8 |
| Dried Milk Solids | 0–20 | 5–10 |
| Corn Syrup Solids | 0.1–15 | 1–4 |
| Glycerine | 0.1–5 | 0.8–1.5 |
| Vanilla/Cream Flavor | 0.1–3 | 0.3–1.2 |
| Lecithin | 0–3 | 0.2–0.8 |
| Salt | 0.1–1.0 | 0.2–0.6 |
| Vitamin $D_3$ (1,000 IU/gram) | 0.01–0.1 | 0.04–0.06 |

All of these batches yielded products which were extruded and cut into pieces calculated to deliver about 500 mg of bioassimilable calcium. The products varied in the degree of tackiness to touch, but all were chewy with a nougat consistency, much like that of a Tootsie Roll, with more than acceptable mouth-feel with at most only a minor amount of chalky texture on chewing. Thus, a nougat product quite acceptable to consumers is produced 1) without driving off excess water, 2) without cooking the material and 3) without spinning the material.

The preferred form of corn syrup is as follows:

CORN SYRUP, a pure, regular D.E. acid-converted syrup, having a level of sweetness and balanced composition of saccharides.

| REPRESENTATIVE CHEMICAL AND PHYSICAL DATA | | | |
|---|---|---|---|
| Essential Properties | | Characteristics | |
| Dextrose Equivalent (DE) | 43 | Appearance | Clear Liquid |
| Baume, Comm (140°/60° + 1) | 43 | Taste | Sweet, Bland |
| Refractive Index (45° C.) | 1.4935 | Odor | Characteristic |
| Total Solids (%) | 80.7 | | |
| Moisture (%) | 19.3 | | |
| Sulfated Ash (%) | 0.3 | | |
| Nitrogen (%) | 0.006 | | |
| PH (1:1) | 4.9 | | |
| Sulphur Dioxide (PPM) | 40 Max. | | |
| Calories/100 g | 316 | | |
| Weight/Volume Factors | | Viscosity (Centipoise) | |
| Specific Gravity (100°/60° F.) | 1.4197 | 80° F. | 81,000 |
| Pounds/Gallon (100° F.) | 11.84 | 90° F. | 40,000 |
| Pounds/Gallon (DSB) | 9.55 | 100° F. | 24,000 |
| | | 110° F. | 11,000 |
| | | 120° F. | 7,000 |
| | | 140° F. | 2,500 |
| Chromatographic Analysis (% Dry Basis) | | | |
| Dextrose | 19 | | |
| Maltose | 14 | | |
| Maltotriose | 12 | | |
| Higher Saccharides | 55 | | |

The resulting method provides a formulation for a composition having an improved texture and having a more creamy and caramel like mouth feel.

CONSUMER TASTE PREFERENCES

A consumer test was conducted with the new formulation. The test used a 9-point liking scales (hedonic scores) as is well known and described in our prior applications and was based on the response of 105 subjects. The higher score indicate a higher preference. The new chocolate formulation identified above was significantly preferred over the old formula with overall score of 6.6 versus 5.0 for the old formula.

Hardness data for our composition was collected for exposure at 40° C. and ambient humidity as listed below. This is assumed to be the worst case condition because the product will dry out at 40° C. The data was collected by using a TA-XT2 Texture Analyser from Texture Technologies Corp. A probe was used that penetrated 3 mm into the sample and the force i n rams was recorded.

| HARDNESS (g) | | | | | |
|---|---|---|---|---|---|
| | Initial | 1 wk | 2 wk | 3 wk | 4 wk |
| New formula | 783 | 1940 | 1464 | 1472 | 2572 |
| Old formula | 3219 | 3754 | NT | NT | >6000* |

* = too hard for the machine  NT = not tested

Clearly as the results indicate the new formulation is superior both to the consumer and in its ability to maintain soft over time. We believe this should enhance the shelf life of the final product. Heretofore in our prior products we preferred not to include a fat, although a fat could have been included had it been desirable. In our new formulation, we found unexpected advantages within incorporating certain types of fat, in order to minimize the stickiness of the resultant composition. It is preferred that the fat component be selected from a list of components having a melting point substantially in the range of 28 to 45 degrees centigrade. We have discovered that in utilizing such a fat, for example hydrogenated coconut oil, partially hydrogenated soybean oil, partially hydrogenated palm kernel oil, partially hydrogenated cottonseed oil or the like or any other vegetable oil or any fat derived emulsifier that exhibits fat mouth feel and texture such as mono or diglycerides or the like, all within the specified range for melting point in the range of 2% to 18% by weight of composition that the fat blooms to the surface of the composition. Normally in the candy industry, for example in the chocolate industry, it is highly undesirable to allow for blooming because it provides an unsavory appearance to the surface of the product. However, we have found that our composition has a desirable shiny surface and we have found that this minimizes the sticking of the composition to the handling equipment and the packaging material. The fat coating also helps to reduce moisture pickup from the air to reduce stickiness. We also have found that the resulting product from the composition stays softer for a longer period of time than our previous formulations and thus enhances the shelf life of the final resultant product.

RESULTS

The resulting composition is uncooked and is substantially free of unbound water therefore having substantially no phase separation for the moisture which much improved consumer preference and expected enhanced shelflife.

Thus, while there have been described what are primarily believed to be the preferred embodiments, those skilled in the art well appreciate that other and further changes and modifications can be made without departing from the true spirit of the invention, and it is intended to include all such changes and modifications within the scope of the claims which are appended hereto.

The embodiments of the invention in which an exclusive property or privilege is claimed are as follows:

1. An uncooked, unspun intimately mixed confectionery composition having sufficient internal cohesively to be handled without losing its integrity as a mass, said composition being substantially free of unbound water and having substantially no phase separation of moisture, comprising:
   (i) a saccharide based component;
   (ii) a hydrated hydrobinding component having a water activity substantially less than about 0.75, in combination with a humectant, said component being hydrated sufficiently to provide controlled water delivery to the saccharide component to provide only enough moisture to bind the ingredients together when mixed and provide internal lubricity for imbibing, delivering and maintaining the moisture in the mass to provide internal cohesivity without losing its integrity as a mass,
   (iii) fat component having a melting point substantially in the range of about 28 to about 45 degrees centigrade for providing a soft yet substantially unsticky chew texture for the composition wherein component (i) is present substantially between about 16%–75% by weight of said composition, component (ii) is present substantially between about 20%–45% by weight of said composition, and wherein component (iii) is present substantially between about 2%–18% by weight of said composition.

2. The composition of claim 1 wherein said hydrated hydrobinding component further comprises at least one material selected from the group consisting of a carbohydrate syrup to impart viscoelasticity to the composition.

3. The composition of claim 2, wherein the carbohydrate syrup is selected from the group consisting of corn syrup, rice syrup, fructose syrup, hydrogenated glucose syrup and combinations thereof.

4. The composition of claim 1 or 2 wherein said fat component is selected from the group consisting of vegetable oils and fat derived emulsifiers that exhibit fat mouth feel and texture all within the specified range for melting point.

5. The composition of claim 4 wherein the fat component blooms to the surface of the composition and provides a shiny finish which minimizes sticking of the composition to equipment and material when handled and packaged.

6. The composition of claim 5 wherein the composition substantially retains its softness over time.

7. The composition of claim 4, wherein the vegetable oil is selected from hydrogenated coconut oil, partially hydrogenated soybean oil, partially hydrogenated palm kernel oil, and partially hydrogenated cottonseed.

8. The composition of claim 4, wherein the emulsifier is selected from the group consisting of mono and diglycerides.

9. The composition of claim 4 further comprising a bioactive agent selected from the group consisting of pharmaceuticals, food, food ingredients, nutritional components nutraceutical, dietary fiber, protein, vitamin, mineral, and herb for effecting a biological and/or chemical response in the body.

10. The composition of claim 1 or 2 further comprising a bioactive agent selected from the group consisting of pharmaceuticals, food, food ingredients, nutritional components nutraceutical, dietary fiber, protein, vitamins mineral, and herb for effecting a biological and/or chemical response in the body.

11. The composition of claim 10, wherein said mineral is calcium.

12. The composition of claim 11, wherein said calcium is present in an amount of up to about 10%–40% by weight of said composition.

13. The composition of claim 11, wherein said calcium is calcium carbonate or calcium citrate.

14. The composition of claim 1, wherein the humectant is selected from group consisting of glycerine and propylene glycol.

* * * * *